US007772209B2

(12) United States Patent
Niyikiza

(10) Patent No.: US 7,772,209 B2
(45) Date of Patent: Aug. 10, 2010

(54) ANTIFOLATE COMBINATION THERAPIES

(75) Inventor: Clet Niyikiza, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 162 days.

(21) Appl. No.: 11/776,329

(22) Filed: Jul. 11, 2007

(65) Prior Publication Data

US 2008/0032948 A1 Feb. 7, 2008

Related U.S. Application Data

(62) Division of application No. 11/288,807, filed on Nov. 29, 2005, now abandoned, which is a division of application No. 10/297,821, filed as application No. PCT/US01/14860 on Jun. 15, 2001, now Pat. No. 7,053,065.

(60) Provisional application No. 60/215,310, filed on Jun. 30, 2000, provisional application No. 60/235,859, filed on Sep. 27, 2000, provisional application No. 60/284,448, filed on Apr. 18, 2001.

(51) Int. Cl.
*A61K 31/70* (2006.01)
*A61K 31/685* (2006.01)
*A61K 31/50* (2006.01)
*A61K 31/525* (2006.01)
*A61K 31/519* (2006.01)

(52) U.S. Cl. ............................ 514/52; 514/77; 514/249; 514/251; 514/265.1

(58) Field of Classification Search .................... 514/52, 514/77, 249, 251, 265.1
See application file for complete search history.

(56) References Cited

U.S. PATENT DOCUMENTS

| 2,920,015 | A | | 1/1960 | Thompson |
| 4,140,707 | A | * | 2/1979 | Cleare et al. ................ 556/137 |
| 5,344,932 | A | | 9/1994 | Taylor |
| 5,405,839 | A | | 4/1995 | Toraya et al. |
| 5,431,925 | A | | 7/1995 | Ohmori et al. |
| 5,563,126 | A | | 10/1996 | Allen et al. |
| 5,736,402 | A | | 4/1998 | Francis et al. |
| 6,207,651 | B1 | | 3/2001 | Allen et al. |
| 6,297,224 | B1 | | 10/2001 | Allen et al. |
| 6,528,496 | B1 | | 3/2003 | Allen et al. |
| 7,053,065 | B2 | | 5/2006 | Niyikiza et al. |
| 2003/0216350 | A1 | | 11/2003 | Allen et al. |
| 2003/0225030 | A1 | | 12/2003 | Allen et al. |
| 2004/0005311 | A1 | | 1/2004 | Pitman |

FOREIGN PATENT DOCUMENTS

EP 0 546 870 6/1993

WO WO 95/27723 10/1995

OTHER PUBLICATIONS

Calvert H.: "Folate status and the safety profile of antifolates", Seminars in Oncology, 2002, 29/2 Suppl. 5, pp. 3-7, XP008005755.
Calvert H.: "Future directions in the development of pemetrexed", Seminars in Oncology, 2002, 29/2 Suppl. 5, pp. 54-61, XP008005744.
Westerhof, et al: "Carrier-and receptor-mediated transport of folate antagonists targeting folate-dependent enzymes: correlates of molecularstructure and biological activity", Mol. Pharmacology, 1995, 48(3), pp. 459-471, XP008005762.
Worzalla, et a]: "Role of folic acid in modulating the toxicity and efficacy of the multitargeted antifolate, LY231514", Anticancer Research (1998), 18(5A), pp. 3235-3239, XP008005757.
Hanauske, et al: "Pemetrexed disodium: A novel antifolate clinically active against multiple solid tumors", Oncologist, Alphamed Press, US, vol. 4, No. 6, 2001, pp. 363-373, XP008005751.
Bunn, et al: "Vitamin B 12 and folate reduce toxicity of Alimta (pemetrexed disodium, LY 231514, MTA), a novel antifolate/antimetabolite", Program/Proceedings—American Society of Clinical Oncology, the Society, US, vol. 76A, No. 20, 2001, p. 300, XPO08005885.
Dierkes, et al., Supplementation with Vitamin B 12 Decreases Homocystein and Methylmalonic Acid but Also Serum Folate in Patients with End-Stage Renal Disease. Metabolism. May 1999. vol. 48, No. 5, pp. 631-635. See: abstract.
Arsenyan et al. (Abstract: Onkol. Nauchn., (1978) 12(10):49-54.
John, et al. (Cancer 2000, 88: 1807-13).
Poydock et al., "Growth-inhibiting effect of hydroxocobaltniin and L-ascorbic acid on two solid tumors in mce", IRCS Medical_ Science, vol. 12, No. 9, pp. 813 (1984).
The Cecil Reference, Textbook of Medicine, 21st Edition (2000). Chapter 198. pp. 1060-1074.
Poydock M. Effect of combined ascorbic acid and B-12 on survival of mice with implanted Ehrlich carcinoma and L1210 leukemia. *Am J Clin Nutr* 1991; 54: 1261S-5S.
Poydock M, et al. Mitogenic inhibition and effect on survival of mice bearing L1210 leukemia using a combination of dehydroascorbic acid and hydroxycobalamin. *Am J Clin Oncol* 1985; 8: 2666-269.
Poydock M, et al. Influence of Vitamins C and B12 on the Survival Rate of Mice Bearing Ascites Tumor. *Expl Cell Biol* 1982; 50:88-91.
Toohey J. Dehydroascorbic acid as an anti-cancer agent. *Cancer Letters* 2008; 263:164-169.
Sallah S, et al. Intrathecal methotrexate-induced megaloblastic anemia in patients with acute leukemia. *Archives of Pathology & Laboratory Medicine* 1999; 123(9): 774-777.
Nishizawa Y, et al. Effects of methylcobalamin on the proliferation of androgen-sensitive or estrogen-sensitive malignant cells in culture and in vivo. *International Journal for Vitamin and Nutrition Research* 1997; 67(3):164-170.

(Continued)

*Primary Examiner*—Kevin Weddington
(74) *Attorney, Agent, or Firm*—Elizabeth A. McGraw

(57) ABSTRACT

A method of administering an antifolate to a mammal in need thereof, comprising administering an effective amount of said antifolate in combination with a methylmalonic acid lowering agent.

22 Claims, No Drawings

OTHER PUBLICATIONS

Tsao C, et al. Influence of cobalamin on the survival of mice bearing ascites tumor. *Pathobiology* 1993; 61(2): 104-.8.

Kamei T, et al. Experimental study of the therapeutic effects of folate, vitamin A, and vitamin B12 on squamous metaplasia of the bronchial epithelium. *Cancer* 1993; 71(8): 2477-83.

Shimizu N, et al. Experimental study of antitumor effect of methyl-B12. *Oncology* 1987; 44(3): 169-73.

Herbert, V. The role of vitamin B12 and folate in carcinogenesis. *Advances in Experimental Medicine and Biology* 1986; 206 (Essent. Nutr. Carcinog.), 293-311.

Kroes A, et al. Effects of 5-fluorouracil treatment of rat leukemia with concomitant inactivation of cobalamin. *Anticancer Research* 1986; 6(4): 737-42.

Kroes A, et al. Enhanced therapeutic effect of methotrexate in experimental rat leukemia after inactivation of cobalamin (vitamin B12) by nitrous oxide. *Cancer Chemotherapy and Pharmacology* 1986; 17(2): 114-20.

Barak A. Vitamin B12 as a possible adjunct in prevention of methotrexate hepatotoxicity. *Biochemical Archives* 1985; 1(3): 139-42.

Herbert V. The inhibition and promotion of cancers by folic acid, vitamin B12, and their antagonists. ACS Symposium Series (1985); 277(Xenobiot. Metab.: Nutr. Eff.), 31-6.

Alimta, NDA 021462, Approved Label of Jul. 2, 2009.

"Clinical Chemistry: principle, procedures, correlations," 3rd edition, 1996, published by Lippincott: pp. 618-627.

Fluorouracil, Physicians Desk References, (c) 1998, pp. 2463-2464.

Hammond, L., et al., "A phase I and pharmacokinetic (PK) study of the multitarget antifol (MTA) LY231514 with folic acid," American Society of Clinical Oncology (ASCO) Meeting Abstract No. 866 (1998).

Kisliuk, RL., 1984. "The Biochemistry of Folates." In Sirotnak (Ed.), Folate Antagonists as Therapeutic Agents. pp. 2-68. Harcourt Brace Jovanovich, Publishers.

Kisliuk, RL., 1999. "Folate Biochemistry in RElation to Antifolate Selectivity." In Jackson (Ed.), Antifolate Drugs in Cancer Therapy. pp. 13-36. Humana Press, New Jersey.

Leucovorin, Physicians Desk Reference, (c) 1999. pp. 1389-1391.

Methotrexate, Physicians Desk Reference, (c) 1999. pp. 1397-1413.

Morgan, et al., "Folic acid supplementation prevent deficient blood folate levels and hyperhomocysteinemia during long-term, low dose methotrexate therapy for rheumatoid arthritis: implications for cardiovascular disease prevent," J. Rheumatol. 25:441-446. (1998).

Niyikiza, C., et al., "LY231514 (MTA): relationship of vitamin metabolite profile to toxicity," American Society of Clinical Oncology (ASCO) Meeting Abstract No. 2139 (1998).

Raltitrexed, The Complete Drug Reference, Martindale, 32nd Ed., Pharmaceutical Press, London, pp. 560, 1990.

Shih, C., et al., "LY231514, a Pyrrolo[2,3-d]pyrimidine-based Antifolate that Inhibits Multiple Folate-requiring Enzymes," Cancer Research. 57:1116-1123. 1997.

Shih, C., et al., "Preclinical Pharmacology Studies and the Clinical Development of a Novel Multitargeted Antifolate, MTA (LY231514)," In Jackson (Ed.), Antifolate Drugs in Cancer Therapy. pp. 13-36 Humana Press, New Jersey, 1998.

Volkov, I., "The master key effect of vitamin B12 in treatment of malignancy—A potential therapy?", Medical Hypotheses. 70:324-328. 2008.

Maysishecheva, N.V., et al.:"AntitumorActivity of Methotrexate When Used in Combination with Cobalamine Derivatives", Eksperimentalnaya Onkologija (1982), vol. 4, No. 5:29-33.

McDonald, A.C., et al.: "Clinical Phase I Study of LY231514, a Multitargeted Antifolate, Administered by Daily x 5 q 21 Schedule", Annals of Oncology (1996), vol. 7:85, Abstract No. 291.

Sofyina, Z.P., et al.: "Possibility of Potentiating the Antineoplastic Action of Folic Acid Antagonist by Methylcobalamine Analogs", Vestnik Akademii Medicinskich Nauk SSSR (1979), vol. 1: 72-78.

\* cited by examiner

ANTIFOLATE COMBINATION THERAPIES

This application is a divisional of application Ser. No. 11/288,807, filed 29 Nov., 2005 now abandoned, which is a divisional of application Ser. No. 10/297,821 filed 12 May, 2002, now U.S. Pat. No. 7,053,065, which claims priority under 35 USC 371, for PCT/US01/14860, filed 15 Jun., 2001, which claims the priority of U.S. provisional applications No. 60/215,310, filed 30 Jun., 2000, No. 60/235,859, filed 27 Sep., 2000, and No. 60/284,448, filed 18 Apr., 2001.

Potentially, life-threatening toxicity remains a major limitation to the optimal administration of antifolates. (see, generally, *Antifolate Drugs in Cancer Therapy*, edited by Jackman, Ann L., Humana Press, Totowa, N.J., 1999.) In some cases, a supportive intervention is routinely used to permit safe, maximal dosing. For example, steroids, such as dexamethone, can be used to prevent the formation of skin rashes caused by the antifolate. (*Antifolate*, pg 197.)

Antifolates represent one of the most thoroughly studied classes of antineoplastic agents, with aminopterin initially demonstrating clinical activity approximately 50 years ago. Methotrexate was developed shortly thereafter, and today is a standard component of effective chemotherapeutic regimens for malignancies such as lymphoma, breast cancer, and head and neck cancer. (Bonnadonna G, Zambetti M, Valagussa P. Sequential or alternating doxorubicin and CMF regimens in breast cancer with more than three positive nodes: Ten year results. JAMA 1995;273(7):542-547; Bonnadonna G, Valagussa P, Moliterni A, Zambetti M, Brambilla C. Adjuvant cyclophosphamide, methotrexate, and fluorouracil in node-positive breast cancer: The results of 20 years of follow-up. N Engl J Med 1995; 332(14):901-906; and Hong W K, Schaefer S, Issell B, et al. A prospective randomized trial of methotrexate versus cisplatin in the treatment of recurrent squamous cell carcinoma of the head and neck. Cancer 1983; 52:206-210.) Antifolates inhibit one or several key folate-requiring enzymes of the thymidine and purine biosynthetic pathways, in particular, thymidylate synthase (TS), dihydrofolate reductase (DHFR), and glycinamide ribonucleotide formyltransferase (GARFT), by competing with reduced folates for binding sites of these enzymes. (Shih C, Habeck L L, Mendelsohn L G, Chen V J, Schultz R M. Multiple folate enzyme inhibition: Mechanism of a novel pyrrolopyrimidine-based antifolate LY231514 (MTA). Advan Enzyme Regul, 1998; 38:135-152 and Shih C, Chen V J, Gossett L S, et al. LY231514, a pyrrolo[2,3-d]pyrimidine-based antifolate that inhibits multiple folate-requiring enzymes. Cancer Res 1997; 57:1116-1123.) Several antifolate drugs are currently in development. Examples of antifolates that have thymidylate synthase inhibiting ("TSI") characteristics include 5-fluorouracil and Tomudex®. An example of an antifolate that has dihydrofolate reductase inhibiting ("DHFRI") characteristic is Methotrexate®. An example of an antifolate that has glycinamide ribonucleotide formyltransferase inhibiting ("GARFTI") characteristics is Lometrexol. Many of these antifolate drugs inhibit more than one biosynthetic pathway. For example Lometrexol is also an inhibitor of dihydrofolate reductase and pemetrexed disodium (Alimta®, Eli Lilly and Company, Indianapolis, Ind.) has demonstrated thymidylate synthase, dihydrofolate reductase, and glycinamide ribonucleotide formyltransferase inhibition.

A limitation to the development of these drugs is that the cytotoxic activity and subsequent effectiveness of antifolates may be associated with substantial toxicity for some patients. Additionally antifolates as a class are associated with sporadic severe mylosuppression with gastrointestinal toxicity which, though infrequent, carries a high risk of mortality. The inability to control these toxicities led to the abandonment of clinical development of some antifolates and has complicated the clinical development of others, such as Lometrexol and raltitrexed. (Jackman A L, Calvert A H Folate-Based Thymidylate Synthase Inhibitors as Anticancer Drugs. Ann Oncol 1995; 6(9):871-881; Laohavinij S, Wedge S R, Lind M J, et al. A phase I clinical study of the antipurine antifolate Lometrexol (DDATHF) given with oral folic acid. Invest New Drugs 1996; 14:325-335; and Maughan T S, James R D, Kerr D, et al., on behalf of the British MRC Colorectal Cancer Working Party. Preliminary results of a multicenter randomized trial comparing 3 chemotherapy regimens (deGramont, Lokich, and raltitrexed) in metastatic colorectal cancer. Proc ASCO 1999; 18:Abst 1007.) Initially, folic acid was used as a treatment for toxicities associated with GARFTI see, e.g. U.S. Pat. No. 5,217,974. Folic acid has been shown to lower homocysteine levels (see e.g. Homocysteine Lowering Trialist's Collaboration. Lowering blood homocysteine with folic acid based supplements: meta-analysis of randomized trials. BMJ 1998; 316:894-898 and Naurath H J, Joosten E, Riezler R, Stabler S P, Allen R H, Lindenbaum J. Effects of vitamin B 12, folate and vitamin B6 supplements in elderly people with normal serum vitamin concentrations. Lancet 1995; 346:85-89), and homocysteine levels have been shown to be a predictor of cytotoxic events related to the use of GARFT inhibitors, see e.g. U.S. Pat. No. 5,217,974. However, even with this treatment, cytotoxic activity of GARFT inhibitors and antifolates as a class remains a serious concern in the development of antifolates as pharmaceutical drugs. The ability to lower cytotoxic activity would represent an important advance in the use of these agents.

Surprisingly and unexpectedly, we have now discovered that certain toxic effects such as mortality and nonhematologic events, such as skin rashes and fatigue, caused by antifolates, as a class, can be significantly reduced by the presence of a methylmalonic acid lowering agent, without adversely affecting therapeutic efficacy. The present invention thus provides a method for improving the therapeutic utility of antifolate drugs by administering to the host undergoing treatment with a methylmalonic acid lowering agent. We have discovered that increased levels of methylmalonic acid is a predictor of toxic events in patients that receive an antifolate drug and that treatment for the increased methylmalonic acid, such as treatment with vitamin B12, reduces mortality and nonhematologic events, such as skin rashes and fatigue events previously associated with the antifolate drugs.

Additionally, we have discovered that the combination of a methylmalonic acid lowering agent and folic acid synergistically reduces the toxic events associated with the administration of antifolate drugs. Although, the treatment and prevention of cardiovascular disease with folic acid in combination with vitamin B12 is known, the use of the combination for the treatment of toxicity associated with the administration of antifolate drugs was unknown heretofore.

The present invention relates to a method of administering an antifolate to a mammal in need thereof, comprising administering an effective amount of said antifolate in combination with a methylmalonic acid lowering agent.

Furthermore, the present invention relates to a method of reducing the toxicity associated with the administration of an antifolate to a mammal comprising administering to said mammal an effective amount of said antifolate in combination with a methylmalonic acid lowering agent.

Furthermore, the present invention relates to a method of inhibiting tumor growth in mammals comprising administering to said mammals an effective amount of an antifolate in combination with a methylmalonic acid lowering agent.

Furthermore, the present invention relates to a method of administering an antifolate to a mammal in need thereof, comprising administering an effective amount of said antifolate in combination with a methylmalonic acid lowering agent and a FBP binding agent. A preferred FBP binding agent is folic acid.

Furthermore, the present invention relates to a method of reducing the toxicity associated with the administration of an antifolate to a mammal comprising administering to said mammal an effective amount of said antifolate in combination with a methylmalonic acid lowering agent and a FBP binding agent. A preferred FBP binding agent is folic acid.

Furthermore, the present invention relates to a method of inhibiting tumor growth in mammals comprising administering to said mammals an effective amount of an antifolate in combination with a methylmalonic acid lowering agent and a FBP binding agent. A preferred FBP binding agent is folic acid.

Furthermore, the present invention relates to the use of a methylmalonic acid lowering agent, alone or in combination with a FBP binding agent, in the preparation of a medicament useful in lowering the mammalian toxicity of an antifolate. A preferred FBP binding agent is folic acid.

Furthermore, the present invention relates to the use of a methylmalonic acid lowering agent in the preparation of a medicament useful in lowering the mammalian toxicity associated with an antifolate, and the medicament is administered in combination with an antifolate.

Furthermore, the present invention relates to the use of a methylmalonic acid lowering agent in the preparation of a medicament useful in lowering the mammalian toxicity associated with an antifolate, and the medicament is administered in combination with an antifolate and a FBP binding agent.

Furthermore, the present invention relates to the use of a methylmalonic acid lowering agent in the manufacture of a medicament for use in a method of inhibiting tumor growth in mammals, which method comprises administering said methylmalonic acid lowering agent in combination with an antifolate.

Furthermore, the present invention relates to a product containing a methylmalonic acid lowering agent, an antifolate and optionally a FBP binding agent as a combined preparation for the simultaneous, separate or sequential use in inhibiting tumour growth.

The current invention concerns the discovery that administration of a methylmalonic acid lowering agent in combination with an antifolate drug reduces the toxicity of the said antifolate drug.

The term "inhibit" as it relates to antifolate drugs refers to prohibiting, alleviating, ameliorating, halting, restraining, slowing or reversing the progression of, or reducing tumor growth.

As used herein, the term "effective amount" refers to an amount of a compound or drug, which is capable of performing the intended result. For example, an effective amount of an antifolate drug that is administered in an effort to reduce tumor growth is that amount which is required to reduce tumor growth.

As used herein, the term "toxicity" refers to a toxic event associated with the administration on an antifolate. Such events include, but are not limited to, neutropenia, thrombopenia, toxic death, fatigue, anorexia, nausea, skin rash, infection, diarrhea, mucositis, and anemia. For further explanation of the types of toxicity experienced by patients receiving antifolates, see, generally, *Antifolate Drugs in Cancer Therapy*. Preferably, toxicity refers to toxic death, fatigue, neutropenia, thrombopenia, and mucositis.

As used herein, the term "nonhematologic event" refers to the occurrence of skin rash or fatigue due to the administration of an antifolate.

As used herein, the term "in combination with" refers to the administration of the methylmalonic acid lowering agent, the antifolate drug, and optionally the folic acid; in any order such that sufficient levels of methylmalonic acid lowering agent and optionally folic acid are present to reduce the toxicity of an antifolate in a mammal. The administration of the compounds maybe simultaneous as a single composition or as two separate compositions or can be administered sequentially as separate compositions such that an effective amount of the agent first administered is in the patient's body when the second and/or third agent is administered. The antifolate drug may be administered to the mammal first, followed by treatment with the methylmalonic acid lowering agent. Alternatively, the mammal may be administered the antifolate drug simultaneously with the methylmalonic acid lowering agent. Preferably, the mammal is pretreated with the methylmalonic acid lowering agent and then treated with the antifolate. If folic acid is to be administered in addition to the methylmalonic acid lowering agent, the folic acid may be administered at any time prior, post, or simultaneously to the administration of either the methylmalonic acid lowering agent or the antifolate. Preferably, the mammal is pretreated with the methylmalonic acid, and then treated with folic acid, followed by treatment with the antifolate compound.

The terms "antifolate" and "antifolate drug" refer to a chemical compound which inhibits at least one key folate-requiring enzyme of the thymidine or purine biosynthetic pathways, preferably thymidylate synthase ("TS"), dihydrofolate reductase ("DHFR"), or glycinamide ribonucleotide formyltransferase ("GARFT"), by competing with reduced folates for binding sites of these enzymes. Preferred examples of antifolates include Tomudex®, as manufactured by Zeneca; Methotrexate®, as manufactured by Lederle; Lometrexol®, as manufactured by Tularik; pyrido[2,3-d]pyrimidine derivatives described by Taylor et al in U.S. Pat. Nos. 4,684,653, 4,833,145, 4,902,796, 4,871,743, and 4,882,334; derivatives described by Akimoto in U.S. Pat. No. 4,997,838; thymidylate synthase inhibitors as found in EPO application 239,362; and most preferred, Pemetrexed Disodium (ALIMTA), as manufactured by Eli Lilly & Co.

The terms "methylmalonic acid" and "MMA" refer to a structural isomer of succinic acid present in minute amounts in healthy human urine.

The term "methylmalonic acid lowering agent" refers to a substrate, which lowers the concentration of methylmalonic acid in a mammal. A preferred example of such a substrate is vitamin B12. For methods of determining methylmalonic acid and substrates therefore, see, e.g., Matchar D B, Feussner J R, Millington D S, et al. Isotope dilution assay for urinary methylmalonic acid in the diagnosis of vitamin B12 deficiency. A prospective clinical evaluation. Ann Intern Med 1987; 106: 707-710; Norman E J, Morrison J A. Screening elderly populations for cobalamin (vitamin B12) deficiency using the urinary methylmalonic acid assay by gas chromatography mass spectrometry. Am J Med 1993; 94: 589-594; Norman E J. Gas Chromatography mass spectrometry screening of urinary methylmalonic acid: early detection of vitamin B12 (cobalamin) deficiency to prevent permanent neurologic disability. GC/MS News 1984; 12:120-129; Martin D C, Francis J, Protetch J, Huff F J. Time dependency of cognitive recovery with cobalamin replacement: report of a pilot study. JAGS 1992; 40: 168-172; Norman E J, Cronin C. Cobalamin deficiency. Neurol 1996; 47: 310-311; Rasmussen K, Moelby I, Jensen M K. Studies on methylmalonic acid in humans; Savage D G, Lindenbaum J, Stabler S P, Allen R H. Sensitivity of methylmalonic acid and total homocysteine determination for diagnosing cobalamin and folate deficiency. Am J Med 1994; 96: 239-246.

The term "vitamin B12" refers to vitamin B12 and its pharmaceutical derivatives, such as hydroxocobalamin, cyano-10-chlorocobalamin, aquocobalamin perchlorate, aquo-10-chlorocobalamin perchlorate, azidocobalamin, chlorocobalamin, and cobalamin. Preferably the term refers to vitamin B12, cobalamin, and chlorocobalamin.

The dosage generally will be provided in the form of a vitamin supplement, namely as a tablet administered orally, such as a sustained release formulation, as an aqueous solution added to drinking water, or as an aqueous parenteral formulation. Preferably the methylmalonic acid lowering agent is administered as an intramuscular injection formulation. Such formulations are known in the art and are commercially available.

The skilled artisan will appreciate that the methylmalonic lowering agents are effective over a wide dosage range. For example, when cobalamin is used as the methylmalonic lowering agent, the dosage of cobalamin may fall within the range of about 0.2 µg to about 3000 µg of cobalamin from once daily for a month to once every nine weeks for a year. Preferably, cobalamin will be dosed as an intramuscular injection of about 500 µg to about 1500 µg administered from about every 24 hours to about every 1680 hours. Preferably, it is an intramuscular injection of about 1000 µg administered initially from about 1 to about 3 weeks prior to administration of the antifolate and repeated from about every 24 hours to about every 1680 hours, regardless of when treatment with the antifolate is started and continued until the administration of the antifolate is discontinued. Most preferred is an intramuscular injection of about 1000 µg administered initially from about 1 to about 3 weeks prior to the first administration of the antifolate and repeated every 6 to 12 weeks, preferably about every 9 weeks, and continued until the discontinuation of the antifolate administrations. However, it will be understood that the amount of the methylmalonic acid lowering agent actually administered will be determined by a physician, in the light of the relevant circumstances, including the condition to be treated, the chosen route of administration, the actual agent administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect.

The term "FBP binding agent" as used herein refers to a folic binding protein binding agent which includes folic acid, (6R)-5-methyl-5,6,7,8-tetrahydrofolic acid, and (6R)-5-formyl-5,6,7,8-tetrahydrofolic acid, or a physiologically-available salt or ester thereof. This latter compound is the (6R)-isomer of leucovorin as disclosed in J. Am. Chem. Soc., 74, 4215 (1952). Both of the tetrahydrofolic acid compounds are in the unnatural configuration at the 6-position. They are 10-20 fold more efficient in binding the folate binding protein compared with their respective (6S)-isomer, see Ratnam, et. al., Folate and Antifolate Transport in Mammalian Cells Symposium, Mar. 21-22, 1991, Bethesda, Md. These compounds are usually prepared as a mixture with their natural form (6S) of diastereomers by non-stereoselective reduction from the corresponding dehydro precursors followed by separation through chromatographic or enzymatic techniques. See e.g. PCT Patent Application Publication WO 880844 (also Derwent Abstract 88-368464/51) and Canadian Patent 1093554. See, e.g. Dietary Reference Intakes for Thiamin, Riboflavin, Niacin, Vitamin B6, Folate, Vitamin B12, Pantothenic Acid, Biotin, and Choline (2000), 8 Folate, pp. 196-305.

"Physiologically-available salt" refers to potassium, sodium, lithium, magnesium, or preferably a calcium salt of the FBP binding agent. "Physiologically-available . . . ester" refers to esters which are easily hydrolyzed upon administration to a mammal to provide the corresponding FBP binding agent free acid, such as $C_1$-$C_4$ alkyl esters, mixed anhydrides, and the like.

The FBP binding agent to be utilized according to this invention can be in its free acid form, or can be in the form of a physiologically-acceptable salt or ester which is converted to the parent acid in a biological system. The dosage generally will be provided in the form of a vitamin supplement, namely as a tablet administered orally, preferably as a sustained release formulation, as an aqueous solution added to drinking water, an aqueous parenteral formulation, e.g., an intravenous formulation, or the like.

The FBP binding agent is usually administered to the subject mammal prior to treatment with the antifolate. Pretreatment with the suitable amount of FBP binding agent from about 1 to about 24 hours is usually sufficient to substantially bind to and block the folate binding protein prior to administration of the antifolate. Although one single dose of the FBP binding agent, preferably an oral administration of folic acid, should be sufficient to load the folate binding protein, multiple dosing of the FBP binding agent can be employed for periods up to weeks before treatment with the active agent to ensure that the folate binding protein is sufficiently bound in order to maximize the benefit derived from such pretreatment.

In the especially preferred embodiment of this invention, about 0.1 mg to about 30 mg, most preferably about 0.3 mg to about 5 mg, of folic acid is administered orally to a mammal about 1 to 3 weeks post administration of the methylmalonic acid lowering agent and about 1 to about 24 hours prior to the parenteral administration of the amount of an antifolate. However, it will be understood that the amount of the methylmalonic acid lowering agent actually administered will be determined by a physician, in the light of the relevant circumstances, including the condition to be treated, the chosen route of administration, the actual agent administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect.

In general, the term "pharmaceutical" when used as an adjective means substantially non-toxic to living organisms.

Methods

To assess the effect of a methylmalonic acid lowering agent, alone or in combination with folic acid on the antitumor efficacy of an antifolate in a human tumor xenograft model, female nude mice bearing human MX-1 breast carcinoma were treated with ALIMTA alone or along with superphysiologic doses of folic acid or vitamin B12 (cobalamin).

The animals were maintained on sterilized standard lab chow ad libitum and sterilized water ad libitum. The human MX-1 tumor cells ($5 \times 10^6$) obtained from donor tumors were implanted subcutaneously in a thigh of female nude mice 8- to 10-weeks old. Beginning on day 7 post tumor cell implantation, the animals were treated with ALIMTA (100 mg/kg or 150 mg/kg) once daily on days 7 through 11 and 14 through 18 by intraperitoneal injection alone or along with folic acid (6 mg/kg or 60 mg/kg) and/or vitamin B12 (165 mg/kg) by intraperitoneal injection on the same schedule.

Tumor response was monitored by tumor volume measurements twice weekly over the course of the experiment. Toxicity was monitored by body weight measurements made at the same time as the tumor volume measurements. Tumor growth delay was the difference in days for the treated and the controls tumors to reach 1000 mm$^3$.

The human MX-1 breast carcinoma xenograft was responsive to treatment with ALIMTA with doses of 100 mg/kg and 150 mg/kg producing tumor growth delays of 17 days and 21 days, respectively. Folic acid was administered to the animals alone at two doses 6 mg/kg and 60 mg/kg on the same schedule as ALIMTA and produced tumor growth delays of 7 days and 12 days, respectively. Vitamin B12 administered alone at a dose of 165 mg/kg resulted in a tumor growth delay of 12 days.

Combinations of ALIMTA at each of the two doses were administered along with each of the vitamins as simultaneous combination regimens. Administration of folic acid (6 mg/kg) along with ALIMTA did not alter the tumor growth delay produced from that obtained with ALIMTA alone. The addition of folic acid at the higher dose (60 mg/kg) along with each dose of ALIMTA resulted in small increases in tumor growth delay to 22 days and 23 days at the ALIMTA doses of 100 mg/kg and 150 mg/kg, respectively. The tumor growth delays with ALIMTA and vitamin B12 (165 mg/kg) treatment were 22 days and 24 days at ALIMTA doses of 100 mg/kg and 150 mg/kg, respectively.

Body weight was used as a general measure of toxicity for each of the treatment regimens. The body weight loss pattern reflected the treatment regimens with weight decrease during the treatment times of days 7 through 11 and 14 through 18 with some weight recovery during the intervening two days. The weight loss due to ALITMA was dose dependent but overall minor (3%). Folic acid alone at either 6 mg/kg or 60 mg/kg did not cause weight loss, in fact folic acid treated animals maintained weight and gained weight over the course of the experiment better than the control animals. The animals treated with ALIMTA (100 mg/kg) and folic acid (60 mg/kg) gained weight (about 20%) over the course of the experiment.

Administration of vitamin B12 did not prevent weight gain in the animals over the time course of the experiment. The animals treated with ALIMTA (100 mg/kg) along with vitamin B12 gained weight while those treated with ALIMTA (150 mg/kg) along with vitamin B 12 maintained weight over the course of the experiment.

In conclusion, administration of super-physiologic but non-toxic doses of the vitamins, folic acid and vitamin B12, did not alter the antitumor activity of ALIMTA in the human MX-1 breast carcinoma xenograft tumor in nude mice and did not increase the toxicity of ALIMTA as determined by body weight measurements of the animals.

The effect of vitamin B12, alone or in combination with folic acid, on antifolates can be demonstrated in standard tests commonly utilized to determine the antitumor activity and toxic effects of the antifolates themselves. In one such test, mice are inoculated with the C3H strain of mammary adenocarcinoma by inserting a 2 mm by 2 mm section of tumor into the axillary region of the mice by trocar. The timing of administering the methylmalonic acid lowering agent, alone or in combination with the folic acid, and the antifolate may be varied. Ten animals are used at each dosage level. Antitumor activity is assessed on day ten (when day one is first dosage of antifolate) by measuring the length and width of the tumor growth using vernier calipers, and the activity is expressed as a percent inhibition of tumor growth.

When the antifolate is administered to infected mice which are maintained on a diet totally free of vitamin B12 and optionally folic acid for two weeks prior to and during treatment, it exhibits moderated antitumor activity at very low doses, but also causes severe toxicity at a very low dose (measured as death of mice).

A test group of mice are maintained on a vitamin B12 and optionally folic acid free diet for two weeks before treatment. Vitamin B12 and optionally folic acid is then administered during the treatment by intramuscular injection of 0.0003% vitamin B12 (weight/volume) and optionally providing the animals drinking water containing 0.0003% folic acid (weight/volume). This concentration translates to about 1.75 mg of vitamin B12 and optionally folic acid per square meter of body surface per day. As the foregoing results indicate, addition of the indicated level of vitamin B12 to the diet of a subject receiving an antifolate results in excellent antitumor activity at low doses, with little or no toxic effects.

The foregoing tests establish that for tumor bearing mice maintained on a vitamin B12 and optionally folic acid free diet prior to and during treatment with an antifolate, the toxicity of the antifolate is very large, with 1 mg/kg/day being lethal to the majority of the mice, and lower antitumor activity is observed at non-toxic drug doses. Very low doses of vitamin B12 partially reverses drug toxicity and improved antitumor activity. Larger doses of vitamin B12 reduce antifolate toxicity even more significantly. Pretreatment of the mouse with vitamin B12 and then administering folic acid prior to administering the antifolate demonstrates a striking reduction in toxicity, almost eliminating the antifolate toxicity completely. Thus, the use of vitamin B12 in combination with an antifolate reduces drug toxicity without adversely affecting antitumor activity, and the use of vitamin B12 in conjunction with folic acid synergistically reduces drug toxicity.

In a typical clinical evaluation involving cancer patients, all of whom have histologically or cytologically confirmed diagnosis of cancer, an antifolate is administered in combination with vitamin B12. Vitamin B12 is administered as a 1000 µg intramuscular injection 1-3 weeks prior to treatment with the antifolate, and 1000 µg intramuscular injection of vitamin B12 is made approximately every 9 weeks until the patient discontinues from therapy. The antifolate is administered in four doses over a two week period by rapid intravenous injection, followed by two weeks of non-therapy. Dosing is made on days 1, 4, 8 and 11 of any two week period. Patients will have an initial course of therapy at a dose of 5 mg/m$^2$/dose, and depending upon the toxic effects observed in the initial course, their subsequent courses may be at the same dose, or may be escalated to 6 mg/m$^2$, or may be attenuated to 4 mg/m$^2$.

In preparation for the foregoing clinical study, pilot studies in humans have established that vitamin B12 given to patients receiving Alimta has effected reduced side effects due to the Alimta. One to two weeks prior to administration of ALIMTA urine is collected and blood is drawn from a human subject; and vitamin metabolite levels, methylmalonic acid and homocysteine, are determined. Homocysteine levels are determined in blood by a fluorescent polarization immunoassay kit manufactured by Abbot Laboratories. Methylmalonic acid levels are determined by urine levels using a 24 hour urine collection kit available from Biolab Medical Unit (a United Kingdom company). Additionally urine and blood may be collected one week prior to administration of ALIMTA (after at least 5 days of folic acid supplementation and at least 1 week vitamin B12 supplementation), and up to 4 days prior to every cycle.

Method of Administration and Dosing Procedures:

1. Folic Acid:

Folic acid will be supplied as one of the following options, with preference in order from option #1 to option #3:
1. 350-600 µg folic acid.
2. A multivitamin containing folic acid in the range of 350 µg to 600 µg is acceptable if option #1 is not available.
3. A dose of folic acid between 350 µg and 1000 µg is acceptable if neither option #1 or option # 2 is available.

For purposes of this study, patients should take oral folic acid daily beginning approximately 1 to 3 weeks before treatment with ALIMTA plus cisplatin or cisplatin alone and continuing daily until discontinuation from study therapy.

2. Vitamin B12

Vitamin B12 will be obtained and administered as a 1000 µg intramuscular injection. A vitamin B12 injection must be administered approximately 1 to 3 weeks before treatment with ALIMTA and should be repeated approximately every 9 weeks until the patient discontinues from study therapy.

Folic acid supplementation, 350-600 µg or equivalent should be taken orally daily beginning approximately 1 to 3 weeks prior to the first dose of MTA plus cisplatin and continue daily until the patient discontinues from study therapy. A vitamin B12 injection, 1000 µg, must be given intramuscularly approximately 1 to 3 weeks prior to the first dose of ALIMTA and should be repeated approximately every 9 weeks until the patient discontinues from study therapy.

Compare presupplementation homocysteine and methylmalonic acid levels to a) the level immediately prior to the initial dose of study drug, and b) to the level immediately prior to the second dose of study drug (i.e., after a full cycle of supplementation), and compare the prevalence of specific toxicities experienced in up to the first seven cycles of therapy in patients who have been supplemented from baseline to the prevalence seen in the earlier patients (n=246) who were not supplemented (Farber et al.)

Toxicity may be compared in specific patients in non-supplemented cycles versus supplemented cycles (cross-over patients).

The data to be compared are:
1) Patient numbers and baseline demographic data for those supplemented from baseline.
2) Homocysteine and methylmalonic acid levels, levels at baseline, prior to first dose, prior to second dose, and prior to each therapy cycle depending of the type of cancer under study.
3) Grade 3 and 4 hematologic toxicity in these fully supplemented patients.
4) Grade 3 and 4 nonhematologic toxicity in these fully supplemented patients.

The grading of toxicities in chemotherapuetic clinical trials is well known to a person of skill in the art. Examples of fatigue and skin rash grading are provided below.

Fatigue Grading—
Neuromotor
Grade 0 none or no change
Grade 1 subjective weakness; no objective findings
Grade 2 mild objective weakness without significant impairment of function
Grade 3 objective weakness with impairment of function
Grade 4 paralysis Rash Grading—
Skin
Grade 0 none or no change
Grade 1 scattered macular or papular eruption or erythema that is asymptomatic
Grade 2 scattered macular or papular eruption or erythema with pruritus or other associated eruption symptoms
Grade 3 generalized symptomatic macular, papular, or vesicular eruption
Grade 4 exfoliative dermatitis or ulcerating dermatitis The vitamins (both folic acid and B12) to be used in the following studies may be obtained from Zenith Gold Line, Centrum, Folvite, or in Canada Apo-Folic. Cyanocobalamin is used as the methylmalonic acid lowering agent in these studies.

Current and past clinical trials show a 4% drug-related death total, 50% grade 3/4 neutropenia, 7% grade 4 thrombocytopenia, and 10% grade 3/4 diarrheas and mucositis in patients administered ALIMTA and folic acid as described in U.S. Pat. No. 5,217,974. Vitamin B12 supplementation with ALIMTA has a moderate effect on drug related toxicity, lowering drug related deaths to 3% and severe toxicities by about 25%. The combination of vitamin B12 and folic acid with ALIMTA has lowered the drug related deaths to <1% in over 480 so treated. The combination of vitamin B12 and folic acid has lowered the drug related grade 3/4 toxic events, see Table 1.

TABLE 1

| | Percent of occurrences prior to B12/folic acid treatment (N = 246) | Percent of occurrences post B12/folic acid treatment (N = 78) |
|---|---|---|
| Hematologic Toxicity/Non-Hematologic Toxicity | 37% | 6.4% |
| Neutropenia | 32% | 2.6% |
| Mucositis | 5% | 1.3% |
| Diarrhea | 6% | 2.6% |
| Neutropenia and Mucositis | 3% | 0% |
| Neutropenia and Diarrhea | 3% | 0% |
| Neutropenia and Infection | 2% | 0% |

Additionally, sixty-two chemonaive patients requiring chemotherapeutic treatment were divided into two groups. Seventeen of these patients received ALIMTA, but did not receive vitamin B12 or folic acid, as described supra. The remaining patients received treatment with vitamin B12, folic acid, and ALIMTA, as described supra. Of patients who received the combination treatment, 8 out of 45 responded to the chemotherapy. Of patients who did not receive the combination treatment, but rather, received only treatment with ALIMTA, only 1 out of 17 patients responded.

I claim:

1. A method for administering pemetrexed disodium to a patient in need thereof comprising administering an effective amount of folic acid and an effective amount of a methylmalonic acid lowering agent followed by administering an effective amount of pemetrexed disodium, wherein
the methylmalonic acid lowering agent is selected from the group consisting of vitamin B12, hydroxycobalamin, cyano-10-chlorocobalamin, aquocobalamin perchlorate, aquo-10-cobalamin perchlorate, azidocobalamin, cobalamin, cyanocobalamin, or chlorocobalamin.

2. The method of claim 1, wherein the methylmalonic acid lowering agent is vitamin B12.

3. The method of claim 2, wherein the vitamin B12 is administered as an intramuscular injection of about 500 µg to about 1500 µg.

4. The method of claim 2, wherein the vitamin B12 is administered as an intramuscular injection of about 1000 µg.

5. The method of claim 2, 3 or 4, wherein the vitamin B12 administration is repeated about every 6 to about every 12 weeks following the administration of vitamin B12 until the administration of the pemetrexed disodium is discontinued.

6. The method of claim 5 wherein the folic acid is administered 1 to 3 weeks prior to the first administration of the pemetrexed disodium.

7. The method of claim 5 wherein the folic acid is administered from about 1 to about 24 hours prior to administration of the pemetrexed disodium.

8. The method according to any one of claims 1-4, wherein between 0.3 mg to about 5 mg of folic acid is administered orally.

9. The method of claim 8 wherein about 350 µg to about 1000 µg of folic acid is administered.

10. The method of claim 9 wherein 350 µg to 600 µg of folic acid is administered.

11. The method of claim 1 further comprising the administration of cisplatin to the patient.

12. An improved method for administering pemetrexed disodium to a patient in need of chemotherapeutic treatment, wherein the improvement comprises:
 a) administration of between about 350 µg and about 1000 µg of folic acid prior to the first administration of pemetrexed disodium;
 b) administration of about 500 µg to about 1500 µg of vitamin B12, prior to the first administration of pemetrexed disodium; and
 c) administration of pemetrexed disodium.

13. The method of claim 12 further comprising the administration of cisplatin to the patient.

14. The method of claim 12, wherein vitamin B12 is administered as an intramuscular injection of about 500 µg to about 1500 µg.

15. The method of claim 14, wherein vitamin B12 is administered as an intramuscular injection of about 1000 µg.

16. The method of claim 15, wherein between 0.3 mg to about 5 mg of folic acid is administered orally.

17. The method of claim 16 wherein about 350 µg to about 1000 µg of folic acid is administered.

18. The method of claim 17 wherein 350 µg to 600 µg of folic acid is administered.

19. The method of claim 18 wherein folic acid is administered 1 to 3 weeks prior to the first administration of the pemetrexed disodium.

20. The method of claim 18 wherein the folic acid is administered from about 1 to about 24 hours prior to administration of the pemetrexed disodium.

21. The method of claim 12, 18, or 19, wherein the vitamin B12 administration is repeated about every 6 to about every 12 weeks following the administration of vitamin B12 until administration of pemetrexed disodium is discontinued.

22. The method of claim 21 further comprising the administration of cisplatin to the patient.

* * * * *

UNITED STATES PATENT AND TRADEMARK OFFICE
CERTIFICATE OF CORRECTION

PATENT NO. : 7,772,209 B2  Page 1 of 1
APPLICATION NO. : 11/776329
DATED : August 10, 2010
INVENTOR(S) : Clet Niyikiza It is certified that error appears in the above-identified patent and that said Letters Patent is hereby corrected as shown below:

Title Page, Col. 2, Line 22, under Other Publications: Delete "Homocystein" and insert --Homocysteine--, therefor.

Title Page, Col. 2, Line 27, under other Publications: Delete "hydroxocobaltniin" and insert --hydroxocobalamin--, therefor.

Title Page, Col. 2, Line 28, under Other Publications: Delete "mce" and insert --mice--, therefor.

Title Page, Col. 2, Line 37, under Other Publications: Delete "2666" and insert --266--, therefor.

Column 1, Line 5, Delete "12 May," and insert --5 Dec.--, therefor.

Column 10, Line 62, In Claim 1, delete "hydroxycobalamin," and insert --hydroxocobalamin,--, therefor.

Column 11, Line 4, In Claim 4, delete "2," and insert --3,--, therefor.

Signed and Sealed this

Twenty-sixth Day of October, 2010

David J. Kappos
*Director of the United States Patent and Trademark Office*